(12) United States Patent
Hofmeyr

(10) Patent No.: US 11,096,821 B2
(45) Date of Patent: Aug. 24, 2021

(54) SYSTEM AND METHOD OF TONGUE AND JAW STABILIZATION

(71) Applicant: Hally Hofmeyr, Victoria (CA)

(72) Inventor: Hally Hofmeyr, Victoria (CA)

(\*) Notice: Subject to any disclaimer, the term of this patent is extended or adjusted under 35 U.S.C. 154(b) by 0 days.

(21) Appl. No.: 16/539,145

(22) Filed: Aug. 13, 2019

(65) Prior Publication Data
US 2021/0045910 A1 Feb. 18, 2021

(51) Int. Cl.
*A61F 5/56* (2006.01)
*A61B 5/00* (2006.01)

(52) U.S. Cl.
CPC ............ *A61F 5/566* (2013.01); *A61B 5/4815* (2013.01); *A61B 5/4818* (2013.01)

(58) Field of Classification Search
CPC .................................................. A61F 5/56–566
USPC ........................................ 128/859–861, 848
See application file for complete search history.

(56) References Cited

U.S. PATENT DOCUMENTS

| | | | | |
|---|---|---|---|---|
| 4,198,967 A * | 4/1980 | Dror | ................. | A61M 16/0493 128/860 |
| 4,304,227 A * | 12/1981 | Samelson | ............... | A61F 5/566 128/848 |
| 4,676,240 A * | 6/1987 | Gardy | ............... | A61M 16/0493 128/848 |
| 5,154,184 A * | 10/1992 | Alvarez | .................. | A61F 5/566 128/848 |
| 5,465,734 A * | 11/1995 | Alvarez | .................. | A61F 5/566 128/848 |
| 6,976,491 B2 * | 12/2005 | D'Agosto | ............... | A61F 5/566 128/200.24 |
| 2009/0126742 A1 * | 5/2009 | Summer | .................. | A61F 5/566 128/848 |

\* cited by examiner

*Primary Examiner* — Daniel J Colilla

(57) ABSTRACT

A system of combined tongue and jaw stabilization is provided. The system comprises a sheath for placement in the human mouth, the sheath of shape and size to accommodate placement of the tongue, and a frontal flange containing holes to facilitate breathing. The system also comprises of at least one extending protuberance attached to the sheath and extending downward from a bottom surface and/or upward from the upper surface of the sheath, to facilitate the retention of the upper and/or lower jaw and hold the device in place. The extending protuberance(s) is a Jaw-stabilizing Nub directed to holding the jaw in a forward position while the sheath holds the tongue in a forward position to maximize and maintain an open upper airway. Retaining ribs are disposed on an inside surface of the sheath, the ribs directed to holding the tongue inside the sheath.

19 Claims, 3 Drawing Sheets

100

200

SYSTEM AND METHOD OF TONGUE AND JAW STABILIZATION

FIELD OF THE INVENTION

The present disclosure is in the field of snoring reduction and sleep aid devices. More particularly, systems and methods described herein provide for gently moving the jaw and tongue forward during sleep, thus opening airways and facilitating more restful sleep.

BACKGROUND

Snoring and sleep apnea are widespread problems. Oral appliances and devices to retain the tongue and promote more clear upper airways have been available since at least the early 1980s. Many attempts, including custom-made devices, have been made to find solutions to such sleep and breathing problems.

Tongue retention devices have traditionally been defined as mouthpieces that retain the tongue and cover the entire upper and lower dental arches with defined mandibular protrusion. The mouthpiece in legacy embodiments pulled the tongue slightly forward because of negative pressure created by displacement of air from the lingual compartment of the device. The mouthpiece was traditionally custom made from casts of the tongue and teeth using soft copolymers.

Custom made tongue retention devices have enjoyed limited success for various reasons including their tendency to tightly restrain the teeth and jaw of the user. Such restraining may cause the jaw muscles to work against the tongue muscle which is also restrained, with the possible result of jaw and/or teeth misalignment. Temporomandibular joint dysfunction (TMJ), pain and compromised movement of the jaw joint and surrounding muscles, may also result.

In recent years, tongue retention devices were designed to merely stabilize the tongue. Like retention devices, the stabilizing devices attach to the tongue by expelling air from the lingual compartment of the device, creating a suction. An objective of this design is to cause the device to be fixed to the tongue only and to hold the tongue in a forward position with the intent to maintain the upper airway while the user is sleeping.

Tongue retention devices and stabilizing devices that came later are restrictive and constraining. Some versions were merely directed to retaining and stabilizing the tongue. Such devices directed primarily or solely to stabilizing the tongue may fall off easily and do not open the airway enough to reduce or eliminate snoring.

Tongue retention devices and stabilizing devices may also cause tongue discomfort and pain and are otherwise uncomfortable because of the excess suction required to bind such devices to the tongue. Bruising and sores or damage to the tongue may result. Such devices also fall off or unbind from the tongue or do not open the airway enough to reduce snoring.

Tongue retention devices and stabilizing devices may need to be custom made for the user and may be expensive. More recent versions, designed for a single size to fit all users, may be available for about $100 and may thus be more affordable.

A further previous implementation, the mandibular advancement device (MAD), moves the mandible forward relative to the maxilla, or upper jaw, to widen the airway to prevent closure. MADs, which are primarily fitted/moulded, professionally or not, to the teeth, and through a hinge mechanism the lower jaw is thrust forward to bring the base of the tongue forward. The intent is to maintain the airway while sleeping, mitigating snoring and obstructive sleep apnea.

But the MAD can cause teeth movement, jaw misalignment and temporomandibular joint dysfunction. Mandibular advancement devices also tend to be custom made and may be uncomfortable and expensive

DETAILED DESCRIPTION

Figure 1:
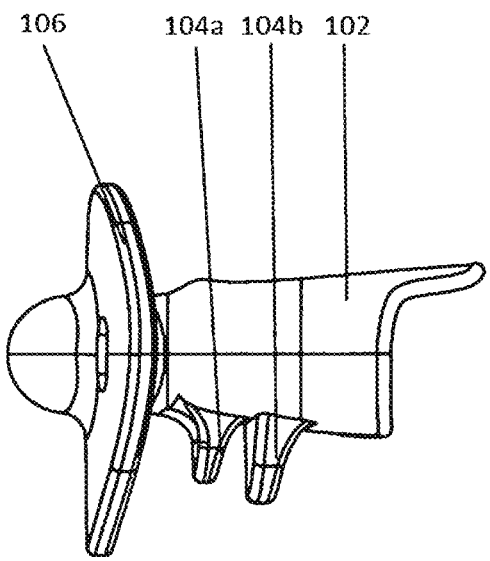
FIG. 1 is a diagram of the tongue and jaw stabilizing device in accordance with an embodiment of the present disclosure.

Systems and methods described herein provide an oral appliance that gently maintains the tongue and jaw in a forward position, allowing the user a more open airway and better sleep. A sheath component accepts insertion of the tongue and holds the tongue in an extended and depressed position.

At least one jaw stabilizing nub, hereinafter "nub", is positioned on the underside of the sheath and extend downward. The nubs are positioned to be behind the user's lower front teeth to hold the mandible or lower jaw in slightly extended position. The two or more nubs provide the user choices as to how far forward he/she wishes his jaw to be positioned. The jaw is allowed to float, preventing the tongue muscle from working against the jaw muscles which could lead to discomfort.

By gently maintaining the jaw and tongue in a forward position, the system opens the airway during sleep. This combined action may reduce the potential for snoring and support improved airflow and more healthy and restful sleep.

The nubs stabilize and suspend the jaw, preventing it from falling back when the jaw relaxes after the user has fallen asleep. Although the jaw is stabilized or suspended, thus preventing the problem of falling back, the jaw is still able to float freely and unconstrained. Discomfort and jaw- and teeth-related issues are far less likely.

The sheath or tongue sleeve has ridges or ribs on its inside surfaces that improve the tongue-retaining capacity. The ridges improve the seal on the tongue and effectively grip the tongue. The ridges reduce the ability of the tongue to dislodge from the sheath and for the appliance to come loose from the user's mouth.

The sheath may be shaped to fit the user's tongue. The thickness of the sheath, the suction created due to air being expelled from the sheath, and the contacting of the tongue by the ridges support the tongue being held in the sheath.

The appliance also includes a lip/gum flange at an outer edge of the sheath. The flange, which has holes for breathing, allows the user to wear the flange outside the lips or between the lips and teeth. In some embodiments, one end of the flange may be worn outside the lips and the other end of the flange may be worn between the teeth and gums.

The appliance may be made from soft silicone and/or related silicone composite polymers. Such materials may allow for comfort, durability, safety, and increased surface tension to reduce the possibility of the device dislodging from its intended placement.

An upper protuberance may be positioned at a front and upper edge of the sheath to assist in holding the device in place. The upper protuberance may also assist in positioning of the device for users with overbite problems.

Users with a wide and varying range of anatomical structures in the upper airway may benefit from systems and methods provided herein. Variations in tongue size and shape, jaw/teeth structure and shape, and oral opening volume may be accommodated. In addition, users that are missing some or all their natural teeth may successfully use the appliance.

Turning to the figures, FIG. 1 is a diagram of the tongue and jaw stabilizing device in accordance with an embodiment of the present disclosure. FIG. 1 depicts components of a system 100 of the tongue and jaw stabilizing device, referred to collectively and for brevity as the device 100. FIG. 1 is a side view of the device 100.

The device 100 comprises a sheath 102, jaw stabilizing nubs or simply nubs 104a-b, and a flange 106. The sheath 102 is hollow and open at its inside end (on the right in FIG. 1) and allows for insertion of the tongue. While not visible in FIG. 1, the sheath 102 includes ridges or ribs on its inside surfaces to assist in holding the tongue as discussed above.

The nubs 104a-b are small protuberances that extend downward from an underside surface of the sheath 102. The nubs 104a-b are positioned behind the lower front teeth of the user and cause the jaw of the user to remain in a forward but floating position. While quantity two nubs 104a-b are shown, in embodiments more than or less than two nubs 104a-b may be in place on the device 100.

In an embodiment, the user could position the device 100 in his/her mouth such that nub 104a is behind his/her lower front teeth. This action would cause the jaw to be maintained in a significantly forward position. If the user desired less of a forward force of the jaw, he/she could position the device such that nub 104b is behind the lower front teeth. Using nub 104b, the jaw would be set less far forward that when using 104a.

While the nubs 104a-b are depicted in FIG. 1 as being of different lengths with nub 104a shorter than nub 104b, in embodiments the nubs 104a-b may be of equal length. In embodiments nub 104a may be longer than nub 104b.

The flange 106 is at the front of the device 100 and may be positioned externally outside the lips or between the lips and teeth. In embodiments, the flange 106 may be positioned by the user partially inside and partially outside his/her mouth.

Figure 2:
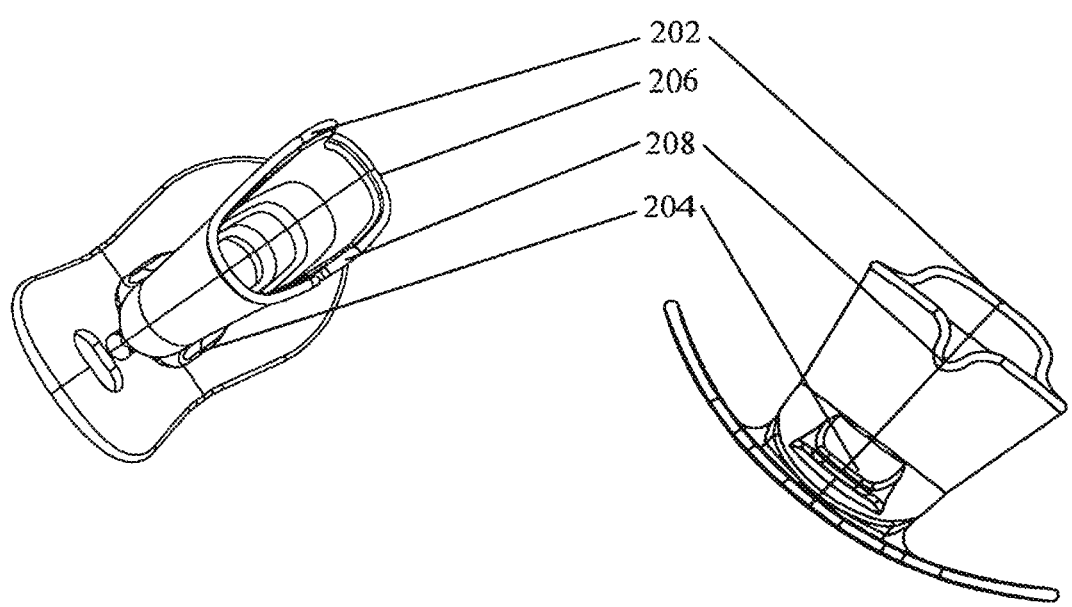
FIG. 2 is a diagram of the tongue and jaw stabilizing device in accordance with an embodiment of the present disclosure.

FIG. 2 is a diagram of the tongue and jaw stabilizing device in accordance with an embodiment of the present disclosure. FIG. 2 depicts components of a device 200 of the tongue and jaw stabilizing device indexed to the components of the system 100.

The view in FIG. 2 is into the open end of the sheath 202 into which the user's tongue is inserted. A single nub 204 and the flange 206 are shown. Also depicted is a V-notch 208 that aids the device 200 in fitting closely with the back area of the underside of the user's tongue.

Figure 3:
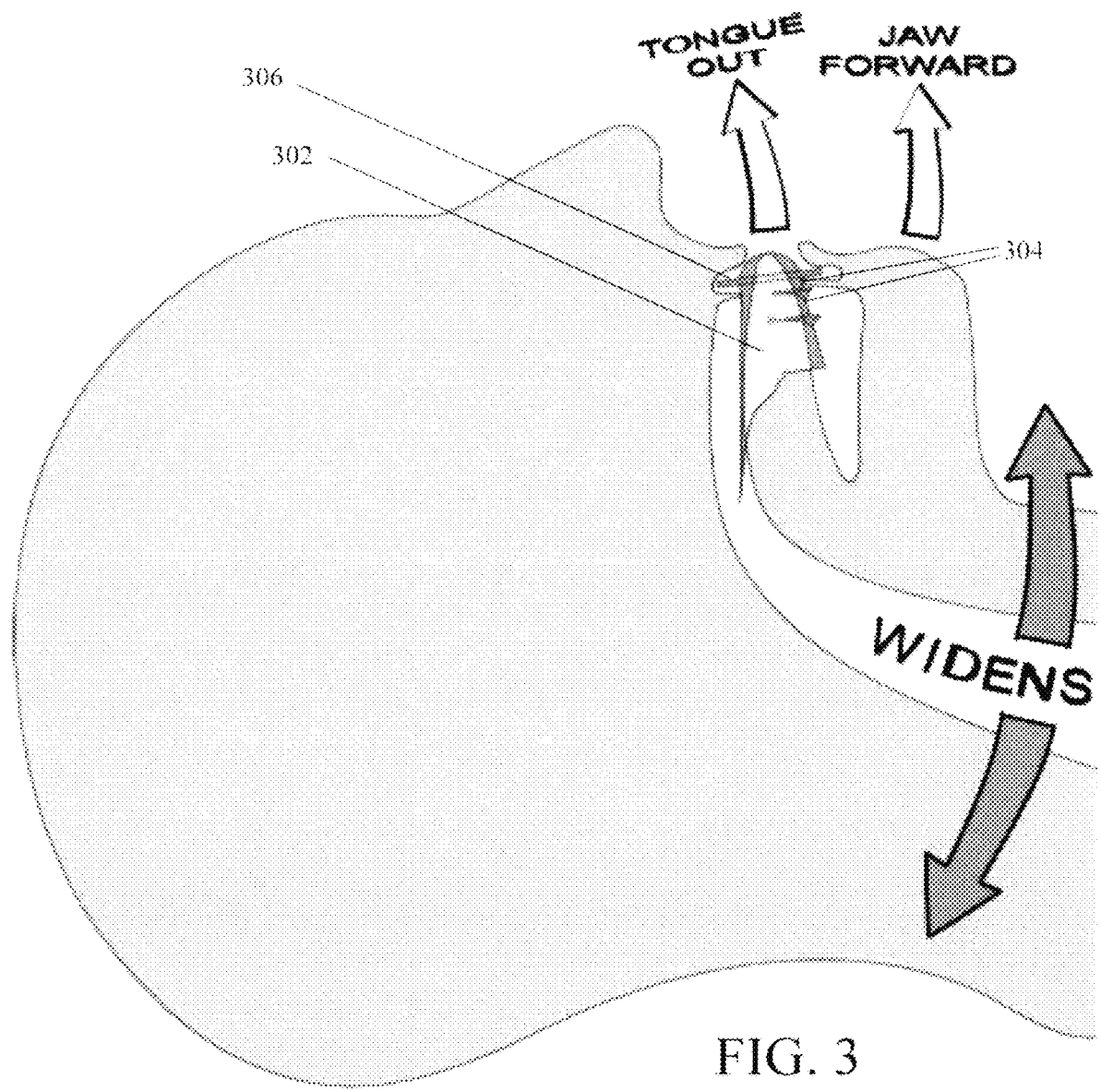
FIG. 3 is a diagram of the tongue and jaw stabilizing device in accordance with an embodiment of the present disclosure.

FIG. 3 is a diagram of the tongue and jaw stabilizing device in accordance with an embodiment of the present disclosure. FIG. 3 depicts components of a device 300 of the tongue and jaw stabilizing device indexed to the components of the system 100.

FIG. 3 depicts an animation of a human head with the device 300 inserted into the mouth. Depicted in FIG. 3 are the sheath 302, nubs 304, and flange 306. FIG. 3 illustrates graphically how placement of the device 300 gently forces the tongue out and the jaw forward with the result of a widened airway, enabling better sleep.

Figure 4:
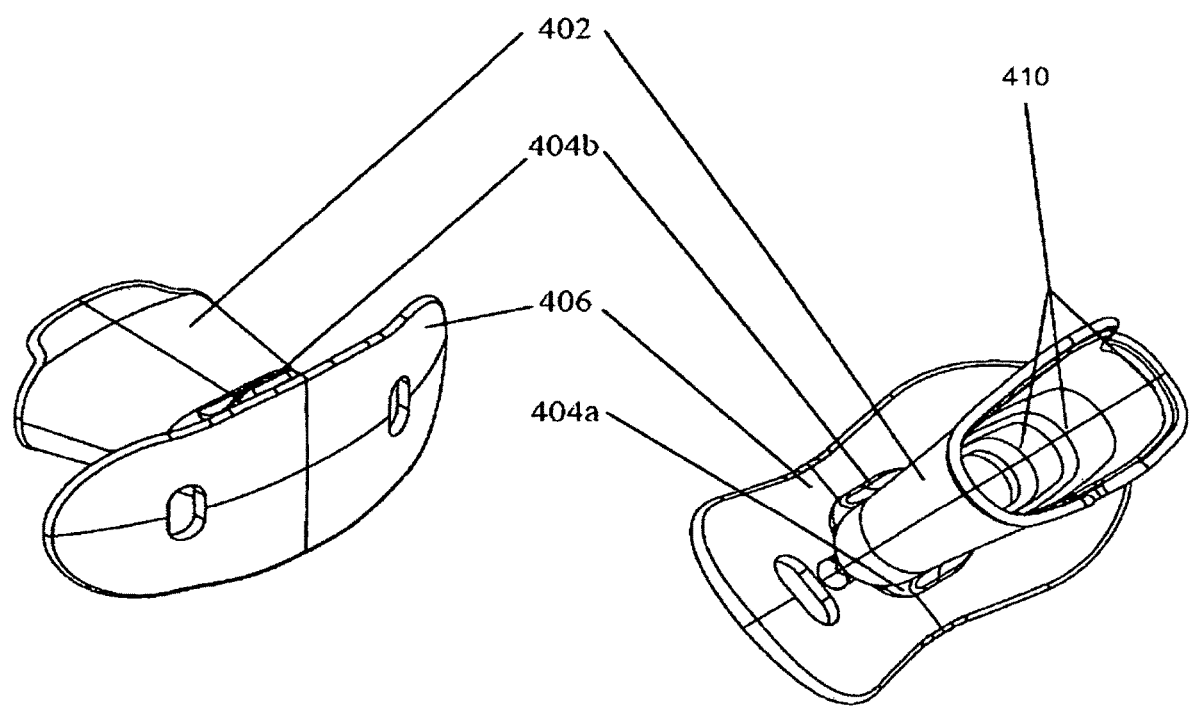
FIG. 4 is a diagram of the tongue and jaw stabilizing device in accordance with an embodiment of the present disclosure.

FIG. 4 is a diagram of the tongue and jaw stabilizing device in accordance with an embodiment of the present disclosure. FIG. 4 depicts components of a device 400 of the tongue and jaw stabilizing device indexed to the components of the system 100. FIG. 4 provides two views of the device 400 with the righthand view depicting the sheath 402, the flange 406, jaw stabilizing nubs 404a and 404b, V-notch 408, and ridges or ribs 410.

Summarizing, the device 100 retains the tongue by holding it through suction and retention ribs. The device 100 simultaneously retains the jaw by means of the nubs 104. The nubs 104 hold the jaw in a forward position, but at the same time allow the jaw to float, which negates issues associated with the tongue retention device, which binds the jaw. By having the tongue retained and the jaw held in a forward position, the ability to open the upper airway may be maximized.

The nubs 104 reduce the common issue of the device 100 falling off easily as with the case of the tongue stabilizing devices. With the nubs 104 there is less need to apply so much suction as with the tongue stabilization devices. This improves comfort, reduces issues with injuring and inflaming the tongue which may result in sores. No custom fitting is required with the device 100 which also helps deal with overbite and underbite.

What is claimed is:

1. A system of tongue and jaw stabilization, comprising:
   a sheath for placement in the human mouth, the sheath of shape and size to accommodate placement of the tongue, wherein the sheath has a lateral width;
   at least one protuberance attached to the sheath and extending downward from a bottom surface of the sheath, wherein the at least one protuberance has a lateral width that does not extend beyond the lateral width of the sheath;
   an upper protuberance disposed at a front outer end of the sheath, the upper protuberance directed to holding the device in place, wherein the upper protuberance has a lateral width that does not extend beyond the lateral width of the sheath; and
   a frontal flange containing holes to facilitate breathing.

2. The system of claim 1, wherein the at least one downward-extending protuberance is a jaw-stabilizing nub directed to holding the jaw in a forward position.

3. The system of claim 1, wherein the sheath holds the tongue in a forward position to maintain open airway.

4. The system of claim 1, wherein retaining ribs are disposed on an inside surface of the sheath, the ribs directed to holding the tongue inside the sheath.

5. The system of claim 1, wherein the system is made from silicone.

6. The system of claim 2, wherein the system further comprises at least two downward-extending protuberances, wherein, the at least two downward-extending protuberances are configured to selectively hold the user's jaw in different positions.

7. The system of claim 1, wherein the flange is configured to be worn either outside a user's lips or between the user's lips and teeth.

8. A method of stabilizing a human tongue and jaw for sleep assistance, comprising:
- a device receiving placement of the tongue into a sheath of the device, wherein the sheath has a lateral width;
- the device holding the tongue forward in the sheath and away from a rear area of a user's mouth;
- the device stabilizing the jaw via first and second protuberances attached to the sheath and extending downward from a bottom surface of the sheath, wherein the first and second protuberances each have a lateral width that does not extend beyond the lateral width of the sheath, and wherein the first and second protuberances are configured to selectively hold a user's jaw in different positions; and
- the device, based at least on holding the tongue forward and stabilizing the jaw, promotes increased opening of a user's airway.

9. The method of claim 8, further comprising retaining ribs disposed on an inside surface of the sheath.

10. The method of claim 9, further comprising the ribs holding the tongue inside the sheath.

11. The method of claim 8, further comprising the device including a flange at an outer edge of the sheath.

12. The method of claim 11, wherein the flange is worn one of outside of lips and between lips and teeth of a user.

13. The method of claim 8, wherein the device is made of silicone.

14. A device for aiding sleep, comprising:
- an oral appliance configured to be placed in a user's mouth;
- the oral appliance comprising:
- a sheath component including ribbed section, wherein the ribbed section is configured to contact a bottom of the user's tongue when the user's tongue is inserted into the sheath component, and wherein the sheath component has a lateral width, and
- two nubs attached to and extending downward from a bottom surface of the sheath component, wherein the two nubs each have a lateral width that does not extend beyond the lateral width of the sheath component.

15. The system of claim 14, wherein ribbed section is disposed on a bottom surface of the sheath component.

16. The system of claim 15, wherein the ribbed section is directed to securing the tongue inside the sheath component.

17. The system of claim 14, wherein the nubs stabilize the jaw and maintain the jaw in a forward position.

18. The system of claim 17, wherein maintenance of the jaw in the forward position facilitates an open airway.

19. The system of claim 14, wherein the oral appliance further comprises a flange configured to be worn either outside a user's lips or between the user's lips and teeth.

* * * * *